US011000065B2

United States Patent
Friedman et al.

(10) Patent No.: US 11,000,065 B2
(45) Date of Patent: May 11, 2021

(54) AEROSOL GENERATION AND EXPOSURE SYSTEM

(71) Applicants: CHARLES R. DREW UNIVERSITY OF MEDICINE AND SCIENCE, Los Angeles, CA (US); THE REGENTS OF THE UNIVERSITY OF CALIFORNIA, Oakland, CA (US)

(72) Inventors: Theodore Friedman, Los Angeles, CA (US); Xuesi Max Shao, Oakland, CA (US)

(73) Assignees: THE REGENTS OF THE UNIVERSITY OF CALIFORNIA, Oakland, CA (US); CHARLES R. DREW UNIVERSITY OF MEDICINE AND SCIENCE, Los Angeles, CA (US)

( * ) Notice: Subject to any disclaimer, the term of this patent is extended or adjusted under 35 U.S.C. 154(b) by 219 days.

(21) Appl. No.: 16/319,814

(22) PCT Filed: Aug. 2, 2017

(86) PCT No.: PCT/US2017/045133
§ 371 (c)(1),
(2) Date: Jan. 22, 2019

(87) PCT Pub. No.: WO2018/026937
PCT Pub. Date: Feb. 8, 2018

(65) Prior Publication Data
US 2019/0262114 A1 Aug. 29, 2019

Related U.S. Application Data

(60) Provisional application No. 62/370,889, filed on Aug. 4, 2016.

(51) Int. Cl.
*A61D 7/00* (2006.01)
*A24F 40/80* (2020.01)
(Continued)

(52) U.S. Cl.
CPC .............. *A24F 40/80* (2020.01); *A61B 5/097* (2013.01); *A61D 3/00* (2013.01); *A61D 7/00* (2013.01);
(Continued)

(58) Field of Classification Search
CPC ........ A61D 7/00; A61D 7/04; A61M 2250/00
See application file for complete search history.

(56) References Cited

U.S. PATENT DOCUMENTS

| 2007/0028918 A1* | 2/2007 | Tsuyuki | A61D 7/04 128/203.12 |
| 2009/0084378 A1* | 4/2009 | Ichikawa | A61D 7/04 128/203.12 |

(Continued)

FOREIGN PATENT DOCUMENTS

EP 2359705 A1 8/2011

OTHER PUBLICATIONS

Patent Cooperation Treaty, International Search Report for PCT/US2017/045133, dated Oct. 26, 2017, pp. 1-2.

*Primary Examiner* — Herbert K Roberts
(74) *Attorney, Agent, or Firm* — Pillsbury Winthrop Shaw Pittman LLP

(57) ABSTRACT

A system is disclosed that includes a holder having a pressurized chamber and configured to secure an aerosol delivery device at least partially within the pressurized chamber. A test chamber is connected to the holder, the test chamber having an inlet allowing an aerosol from the aerosol delivery device to enter the test chamber.

17 Claims, 3 Drawing Sheets

(51) Int. Cl.
*A61D 3/00* (2006.01)
*G01N 1/22* (2006.01)
*G01N 33/00* (2006.01)
*A61B 5/097* (2006.01)
*A61M 16/00* (2006.01)
*A61M 16/10* (2006.01)
*A61M 15/06* (2006.01)
*A61M 16/20* (2006.01)

(52) U.S. Cl.
CPC ........... *G01N 1/22* (2013.01); *G01N 33/0016* (2013.01); *A61M 15/06* (2013.01); *A61M 16/10* (2013.01); *A61M 16/20* (2013.01); *A61M 2016/0027* (2013.01); *A61M 2016/0039* (2013.01); *A61M 2209/02* (2013.01)

(56) References Cited

U.S. PATENT DOCUMENTS

2011/0011160 A1  1/2011  Gerde
2017/0000082 A1* 1/2017  Cole ................ A61D 7/04

* cited by examiner

310 — Securing aerosol delivery device at least partially within holder that includes pressurized chamber 320 — Activating aerosol delivery device to cause aerosol to be emitted from aerosol delivery device 330 — Transferring aerosol from aerosol delivery device to test chamber by at least pressurizing the pressurized chamber with pressurized gas source

Fig. 3

AEROSOL GENERATION AND EXPOSURE SYSTEM

RELATED APPLICATIONS

This patent application is a national stage entry of, and claims priority to International Patent Application No. PCT/US2017/045133 filed Aug. 2, 2017, which claims the benefit of U.S. Provisional Application No. 62/370,889, filed Aug. 4, 2016. The entire contents of the foregoing applications are incorporated herein by reference, including all text and drawings.

STATEMENT REGARDING FEDERALLY SPONSORED RESEARCH OR DEVELOPMENT

This invention was made with government support under grant number 2R24DA017298 awarded by the National Institutes of Health. The government has certain rights in the invention.

BACKGROUND

Electronic cigarettes deliver nicotine to users without burning tobacco. Electronic cigarette use has rapidly proliferated worldwide. As electronic-cigarettes are relatively new products, their health benefits and risks are subjects of public health disputes. Electronic cigarette smoke is an aerosol, defined as a suspension of small particles in air, and not merely nicotine vapor as incorrectly claimed by the industry. Mainstream and secondhand electronic cigarette aerosols may contain, in addition to nicotine and propylene glycol or glycerin, detectable levels of toxins including carcinogens and heavy metals such as cadmium and lead.

SUMMARY

A system is disclosed that includes a holder having a pressurized chamber and configured to secure an aerosol delivery device at least partially within the pressurized chamber. A test chamber is connected to the holder, the test chamber having an inlet allowing an aerosol from the aerosol delivery device to enter the test chamber.

In some variations, one or more of the following features can be included in any feasible combination.

In some implementations, a pressurized gas source can be operatively connected to the pressurized chamber allowing gas in the pressurized gas source to fill the pressurized chamber and cause the aerosol emitted from the aerosol delivery device to transfer from the pressurized chamber to the test chamber.

The holder can also be part of a number of holders. The holder can be configured to cause the aerosol delivery device to extend into the test chamber. A multichannel valve can be configured to selectively direct gas from the pressurized gas source to at least one of the holders.

There can be a path directing the pressurized gas to the test chamber without passing through the pressurized chamber. A valve can selectively direct the gas to either the holder or to the test chamber through the path.

In other implementations, the aerosol delivery device can be an electronic cigarette.

In an interrelated aspect, a method is disclosed that includes securing an aerosol delivery device at least partially within a holder comprising a pressurized chamber. Also, the aerosol delivery device is activated to cause aerosol to be emitted from the aerosol delivery device. The aerosol is transferred from the aerosol delivery device to a test chamber by at least pressurizing the pressurized chamber with a pressurized gas source.

In some implementations, the method can include pressurizing the pressurized chamber to have a pressure greater than the test chamber. The pressure can cause the aerosol to transfer from the aerosol delivery device to the test chamber through the aerosol delivery device. The pressurized chamber can be pressurized to between 1 and 200 psi.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 3 is a diagram illustrating a method in accordance with certain aspects of the present disclosure.

DETAILED DESCRIPTION

Testing aerosol generation devices or conducting laboratory research on subjects exposed to aerosols can include introducing an aerosol to a test subject in a controlled manner. The present disclosure describes, among other things, implementations for aerosol delivery systems and a test chamber that can be used to expose animals or other test subjects to an aerosol. For example, pressurizing one end of an aerosol delivery device can cause the aerosol to emit from the other end of the aerosol delivery device and go into the test chamber. In some implementations, the systems described herein can include electronic aerosol delivery device activation and control units as well as a test chamber being configured to hold free-moving animals.

As used herein, the term "aerosol delivery device" refers to any type of electronic cigarette, conventional cigarette, or other source of aerosol, gas, or compound that can be provide an aerosol, as described below.

Also as used herein, the term "aerosol" refers to any gas or compound that is generated by or emitted from an aerosol delivery device. For example, an aerosol can include smoke or vapor from an E-cigarette, smoke from a conventional cigarette, or any other type of gas or emission emitted or generated from any type of device. Therefore, even though as used herein the term "aerosol" is typically referenced with regard to vapor from an electronic cigarette, such references should not be considered as excluding other implementations.

Figure 1:
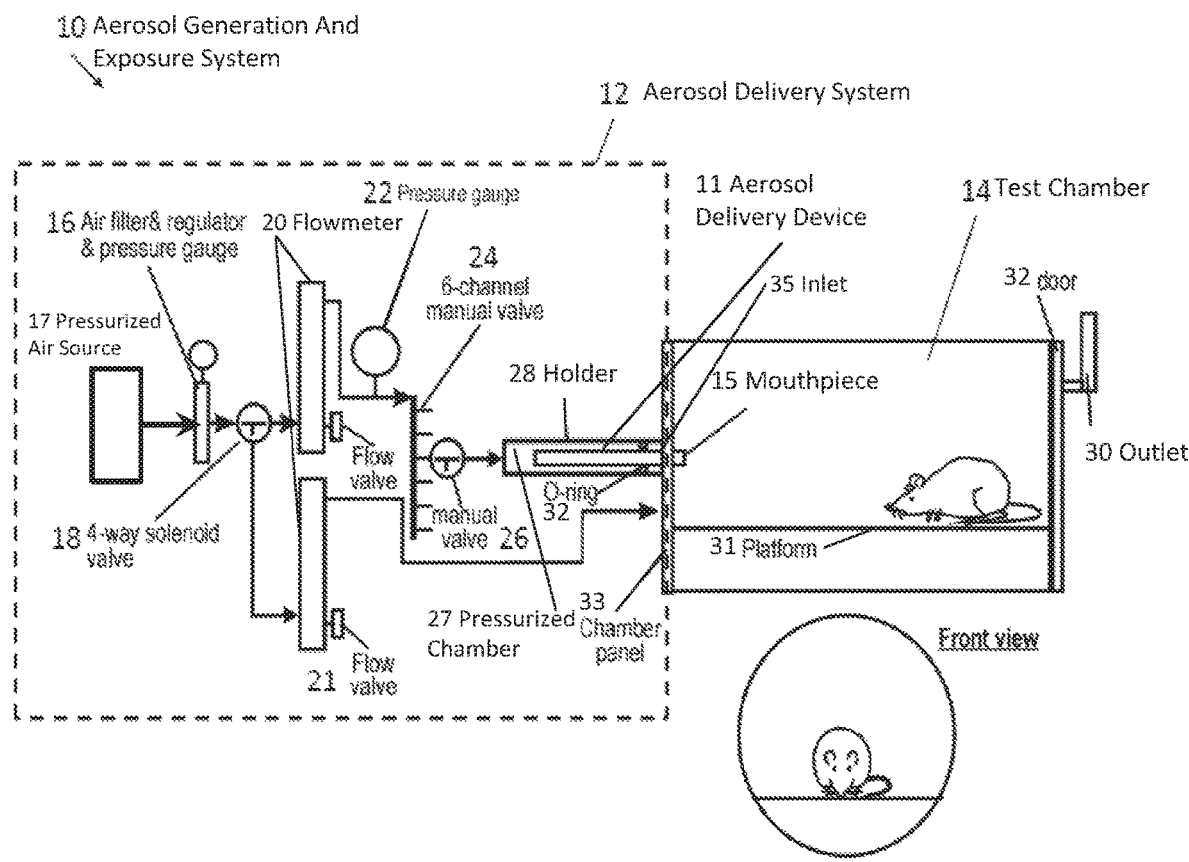
FIG. 1 is a diagram illustrating an aerosol generation and exposure system in accordance with certain aspects of the present disclosure.

FIG. 1 is a diagram illustrating an aerosol generation and exposure system 10 (also referred to herein as system 10) in accordance with certain aspects of the present disclosure. System 10 can include aerosol delivery system 12 for delivery of an aerosol into test chamber 14, where, for example, the aerosol can be measured or introduced to a test subject.

Some implementations of aerosol delivery system 12 can include regulator 16, valve 18, flowmeter 20, pressure gauge 22, multi-channel valve 24, at least one manual valve 26, and at least one holder 28 for holding aerosol delivery device 11. Further details of some components of aerosol delivery system 12 are discussed in greater detail below.

Aerosol delivery system 12 can include holder 28 that can be configured to secure aerosol delivery device 11. In some embodiments, holder 28 can include a mechanism, such as O-ring 32 or foam insert, that allows for universal fit regardless of aerosol delivery device 11 type or shape.

Holder 28 can also include a pressurized chamber 27 shaped to contain at least part of aerosol delivery device 11. Pressurized chamber 27 can receive gas from pressurized gas source 17 and therefore can have a higher pressure than other components in the system, for example test chamber 14. As used herein, the term "pressurized chamber" does not imply or require that the pressurized chamber is pressurized at all times or pressurized to any particular pressure. The term "pressurized chamber" is intended only to distinguish this chamber from other chambers described herein and the note that in some implementations, the pressurized chamber can be pressurized (either higher or lower) relative to other parts of system 10.

Holder 28 can secure aerosol delivery device 11 partially within pressurized chamber 27. The remainder of aerosol delivery device 11 can extend into test chamber 14. As shown in FIG. 1, aerosol delivery device 11 can include a mouthpiece 13. Mouthpiece 13 can extend partially or wholly into test chamber 14. Aerosol from aerosol delivery device 11 can be introduced into test chamber 14 through mouthpiece 13. Mouthpiece 13 can be any kind of mouthpiece, for example that used with electronic cigarettes. Mouthpiece 13 can be attached to a tank of aerosol delivery device 11 so as to receive aerosol when aerosol delivery device 11 is activated. In other implementations, holder 28 can hold aerosol delivery device 11 entirely within holder 28. In these implementations, test chamber 14 can include inlet 35, an aperture, or a conduit, between pressurized chamber 27 and test chamber 14 to allow aerosol to pass between the two chambers.

In other implementations, as shown in FIG. 1, aerosol delivery system 12 can include multiple holders (though only holder 28 is depicted in FIG. 1) connected to multi-channel valve 24. Each of the holders can have their own corresponding aerosol delivery device 11. In some implementations, different types of aerosol delivery devices can be in different holders to allow different types or amounts of aerosol to be introduced into test chamber 14.

In some implementations, pressurized gas source 17 can be operatively connected to pressurized chamber 27 to allow gas in pressurized gas source 17 to fill pressurized chamber 27. This can cause the aerosol emitted from aerosol delivery device 11 to transfer from pressurized chamber 27 (or aerosol delivery device 11 at least partially in pressurized chamber 27) to the test chamber 14. Pressurized gas source 17 can include, for example, a gas bottle, a canister, a cylinder, a line or other conduit that is connected to a source of gas, a fan, a pump, or another device that creates a pressure differential by virtue of its operation or a gas contained therein. Though some implementations described herein refer to pressurized gas source 17 being at a higher pressure than other locations in system 10, it is also contemplated that the pressurized gas source 17 can provide a lower pressure than other locations in system 10, generally reversing the operations and gas flows described herein. The gas can include, for example, air, oxygen, nitrogen, or any other gas or vaporous compound.

Aerosol delivery system 12 can include connected components to direct a controlled flow of gas through at least one aerosol delivery device to dispense aerosol into test chamber 14. The connections in aerosol delivery system 12 can be enabled by any suitable means, such as a series of interconnected metal, rubber, or plastic tubing. The flow of gas into aerosol delivery system 12 can be regulated by regulator 16. Regulator 16 can be any suitable regulator capable of accurate control over the pressure of incoming gas. In some embodiments, regulator 16 is capable of controlling the pressure of incoming gas, such as over a range of 1 to 200 psi and in increments of 1 to 10 psi. In some implementations, regulator 16 can include an air filter. In other implementations, regulator 16 can also include a pressure gauge.

Aerosol delivery system 12 can also include valve 18 downstream from regulator 16. Valve 18 can be, for example, any suitable solenoid valve such as a four-way solenoid valve. Valve 18 can selectively direct the gas to either holder 28 or to test chamber 14 along at least two paths: a first path directing the gas to the test chamber without passing through the pressurized chamber or a second path through aerosol delivery device 11 for aerosol generation. In some implementations, the first path can also include a flowmeter 20, a flow valve 21, a pressure gauge 22, or any combination thereof to monitor and/or control the flow rate of gas into test chamber 14. In other implementations, the second path further comprises a flowmeter 20, a flow valve 21, or both to monitor and/or control the flow rate of gas into test chamber 14.

As shown in FIG. 1, when directing gas through aerosol delivery device 11, gas can go from solenoid valve 18 into multi-channel valve 24. Multichannel valve 24 can be configured to selectively direct gas from the pressurized gas source to any number of holders 28. Multi-channel valve 24 can have any suitable number of channels, including but not limited to 1, 2, 3, 4, 5, 6, 7, 8, 9, and 10 or more channels. The channels can have attachments for at least one manual valve 26, such that the flow of gas in each channel may be individually controlled. Each manual valve 26 can be connected to one holder 28. Each holder 28 can be connected to the interior of test chamber 14, such that gas flowing through each holder 28 may pass through a held aerosol delivery device 11 to dispense aerosol into test chamber 14.

As shown in FIG. 1, test chamber 14 can be connected to holder 28, for example at chamber panel 33. Test chamber 14 can include inlet 35 allowing an aerosol from aerosol delivery device 11 to enter test chamber 14. Test chamber 14 further can also include at least one outlet 30 to permit displaced air to exit test chamber 14. In some implementations, the outlet can include an outlet filter. Test chamber 14 can have any suitable size or shape. In some implementations, test chamber 14 can have the shape of a box. In other implementations, test chamber 14 is can have the shape of a cylinder. In various implementations, test chamber 14 can be appropriately sized to fit the dimensions of a desired test animal. In some implementation, test chamber 14 can be a cylinder having a diameter of 7 to 8 inches and a length of 10 inches. Test chamber 14 can be constructed from any suitable material, including plastics and metals. In certain embodiments, test chamber 14 can include at least one transparent region to permit observation of any animals enclosed within. Platform 31 can be disposed in test chamber 14 to support any animals or test subjects.

The systems described herein can be made using any suitable method known in the art. The methods may vary depending on the materials used. For example, devices substantially comprising a plastic or polymer may be milled from a large block or injection molded. Likewise, devices substantially comprising a metal may be milled, cast, etched, or deposited by techniques such as chemical vapor deposition, spraying, sputtering, and ion plating. In some embodiments, the devices may be made using 3D printing techniques commonly used in the art.

Two experimental examples are provided that illustrate results that can occur with the use of the system 10. The first example describes a comparison of aerosol particle diameter distributions at a mouthpiece of the aerosol delivery device 11 to the aerosol measured elsewhere in the test chamber. The second example describes an aerosol exposure experiment on a test subject.

Figure 2:
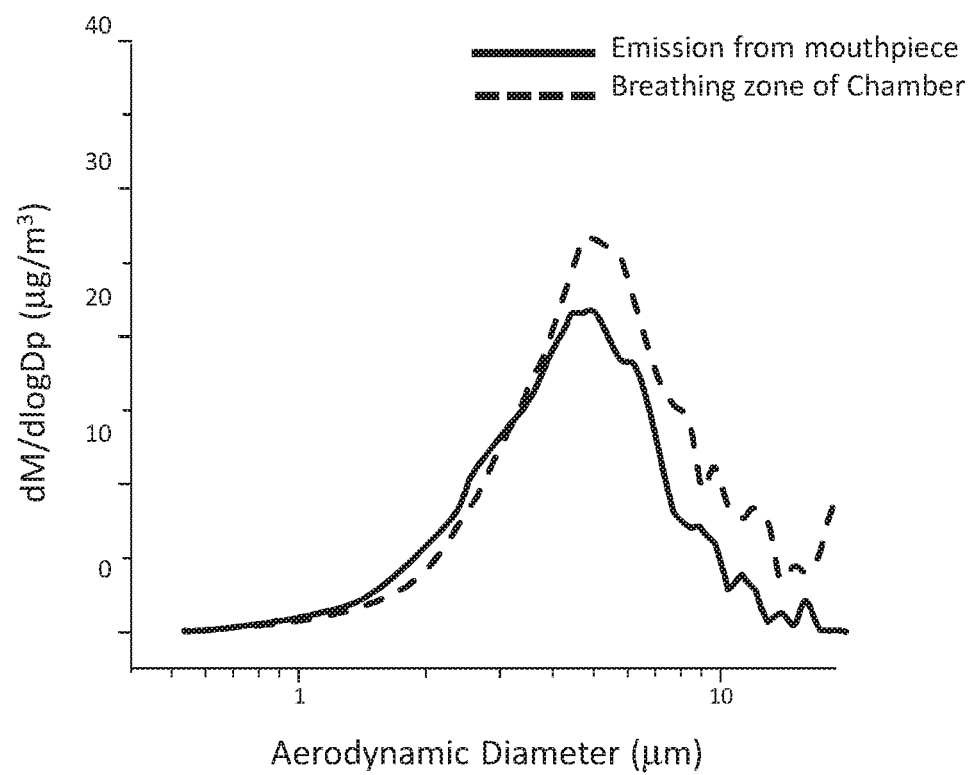
FIG. 2 is a graph illustrating an example of experimental results for mass density versus an aerodynamic diameter in accordance with certain aspects of the present disclosure.

FIG. 2 is a graph illustrating an example of experimental results for mass density versus an aerodynamic diameter in accordance with certain aspects of the present disclosure. An aerodynamic particle sizer was used to measure the droplet size distribution of an aerosol from an electronic cigarette. One electronic cigarette was used for these tests. 2-3 seconds after the start of a 9 second period of electronic cigarette activation, 6-second samples were taken. The distribution curves shown in FIG. 2 are averages of the 6-second samples. The solid line is direct emission samples collected close to the outlet of the mouthpiece of the electronic cigarette tank. The dashed line shows samples collected in the breathing zone of the animal system (generally the interior of test chamber 14 and not necessarily near the aerosol delivery device 11).

The mass concentrations in air in the breathing zone of the system were measured to be 0.76 mg/L when one electronic cigarette was activated and 2.56 mg/L when 2 E-cigarettes were activated (measured with a one-stage cascade impactor). The mass median aerodynamic diameter (MMAD) is 4.37±0.406 µm (mean±SD) for the direct emission samples and 5.33±0.464 µm for the breathing zone samples. These results demonstrate that the characteristics of electronic cigarette aerosol in the breathing zone of rodents are similar to those inhaled into the respiratory system of electronic cigarette smokers.

An electronic cigarette exposure experiment was performed on 9 mice using the system. Electronic cigarette aerosol generation and exposure parameters were: activation of one electronic cigarette, 4 seconds per puff, one puff every 20 sec, 10 puffs per episode (200 seconds per episode), one episode every 30 min, 4 episodes in 2 hours. Mouse plasma nicotine concentration was 35.3±20.0 ng/ml (mean±SD) and plasma cotinine (a nicotine metabolite) was 116±9.9 ng/ml. The plasma concentrations of nicotine and cotinine are close to those of human tobacco smokers.

FIG. 3 is a diagram illustrating a method in accordance with certain aspects of the present disclosure.

At 310, aerosol delivery device 11 can be secured at least partially within holder 28 that includes pressurized chamber 27.

At 320, aerosol delivery device 11 can be activated to cause aerosol to be emitted from aerosol delivery device 11.

At 330, the aerosol can be transferred from aerosol delivery device 11 to test chamber 14 by at least pressurizing pressurized chamber 14 with pressurized gas source 17.

In some implementations, a method can include pressurizing pressurized chamber 27 to have a pressure greater than test chamber 14. This pressure can cause the aerosol to transfer from aerosol delivery device 11 to test chamber 14 through the aerosol delivery device 11. In other implementations, the method can also include pressurizing pressurized chamber 14 to between 1 and 200 psi.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention (s), and their equivalents, that are protected thereby.

What is claimed is:

1. A system comprising:
   a pressurized gas source configured to generate a flow of gas;
   a regulator configured to receive and regulate the flow of gas from the source, the regulator comprising a filter configured to filter the flow of gas from the gas source and a first pressure gauge configured to determine a pressure of the flow of gas from the source;
   a multi-way solenoid valve configured to receive the flow of gas after passing through the regulator, the solenoid valve configured to selectively direct the flow of gas along a first pathway and a second pathway,
   wherein the first pathway comprises:
      a flowmeter configured to determine a flow rate of the flow of gas in the first pathway;
      a second pressure gauge configured to determine a pressure of the flow of gas in the first pathway;
      a multichannel manual valve configured to selectively direct gas from the second pathway to at least one of a plurality of holders;
      at least one holder configured to receive the flow of gas from the multichannel manual valve through a channel linking the multichannel manual valve and the holder, the channel comprising an individual manual valve configured to control the flow of gas through the channel to the holder, the holder comprising a chamber pressurized by the flow of gas and an aerosol delivery device secured at least partially within the pressurized chamber; and a test chamber connected to the holder, the test chamber comprising an inlet allowing an aerosol from the aerosol delivery device to enter the test chamber; and wherein the second pathway comprises a different channel that leads to the test chamber without passing through the chamber pressurized by the flow of gas or the aerosol delivery device.

2. The system of claim 1, wherein:
the flow of gas is configured to fill the pressurized chamber and cause the aerosol emitted from the aerosol delivery device to transfer from the pressurized chamber to the test chamber.

3. The system of claim 1, further comprising the plurality of holders, the plurality of holders comprising the holder.

4. The system of claim 1 wherein the holder is configured to cause the aerosol delivery device to extend into the test chamber.

5. The system of claim 1 wherein the aerosol delivery device is an electronic cigarette.

6. A method comprising:
generating a flow of gas with a gas source;
receiving, regulating, and filtering the flow of gas with a regulator;
determining a pressure of the flow of gas from the gas source with a first pressure gauge;
receiving, with a multi-way solenoid valve, the flow of gas after the regulating, filtering, and pressure determination;
selectively directing, with the solenoid valve, the flow of gas along a first pathway and a second pathway,
wherein selectively directing the flow of gas along the first pathway comprises:
determining a flow rate of the flow of gas in the first pathway with a flowmeter:
determining a pressure of the flow of gas in the first pathway with a second pressure gauge;
selectively directing, with a multichannel manual valve, gas from the second pathway to at least one of a plurality of holders;
receiving, with at least one holder, the flow of gas from the multichannel manual valve through a channel linking the multichannel manual valve and the holder, the channel comprising an individual manual valve configured to control the flow of gas through the channel to the holder;
securing an aerosol delivery device at least partially within the holder, the holder comprising a pressurized chamber;
activating the aerosol delivery device to cause aerosol to be emitted from the aerosol delivery device; and
transferring the aerosol from the aerosol delivery device to a test chamber by at least pressurizing the pressurized chamber with the flow of gas; and
wherein selectively directing the flow of gas along the second pathway comprises directing the flow of gas to the test chamber in a different channel without passing through the chamber pressurized by the flow of gas or the aerosol delivery device.

7. The method of claim 6, further comprising:
pressurizing the pressurized chamber to have a pressure greater than the test chamber, the pressure causing the aerosol to transfer from the aerosol delivery device to the test chamber through the aerosol delivery device.

8. The method of claim 6 wherein the pressurized chamber is pressurized to between 1 and 200 psi.

9. The system of claim 1, wherein the different channel of the second pathway leads to the test chamber without passing through the flowmeter, the second pressure gauge, the multichannel manual valve, the individual manual valve, the pressurized chamber, or the aerosol delivery device.

10. The system of claim 9, wherein the second pathway comprises a second flowmeter configured to determine a flow rate of the flow of gas in the different channel.

11. The system of claim 1, wherein the solenoid valve is a four-way solenoid valve.

12. The system of claim 1, wherein the test chamber comprises a platform configured to support a test subject inside the test chamber.

13. The system of claim 12, wherein the test chamber further comprises a door for the test subject.

14. The system of claim 13, wherein the test chamber further comprises an outlet configured to permit displaced gas to exit the test chamber.

15. The system of claim 1, wherein the aerosol delivery device comprises a mouthpiece that protrudes into the test chamber.

16. The method of claim 6, further comprising providing a platform configured to support a test subject inside the test chamber, and providing a door for the test subject.

17. The method of claim 16, further comprising providing an outlet in the test chamber configured to permit displaced gas to exit the test chamber.

* * * * *